(12) United States Patent
Karperien et al.

(10) Patent No.: US 9,132,201 B2
(45) Date of Patent: *Sep. 15, 2015

(54) HYDROGELS BASED ON POLYMERS OF DEXTRAN TYRAMINE AND TYRAMINE CONJUGATES OF NATURAL POLYMERS

(75) Inventors: Hermanus Bernardus Johannes Karperien, Eibergen (NL); Rong Jin, Enschede (NL); Liliana Sofia Moreira Teixeira, Enschede (NL); Jan Feijen, Hengelo (NL); Pieter Jelle Dijkstra, Borne (NL)

(73) Assignee: UNIVERSITY OF TWENTE, INSTITUTE FOR BIOMEDICAL AND TECHNICAL MEDICINE (MIRA), Enschede (NL)

( * ) Notice: Subject to any disclaimer, the term of this patent is extended or adjusted under 35 U.S.C. 154(b) by 155 days.

This patent is subject to a terminal disclaimer.

(21) Appl. No.: 13/509,365

(22) PCT Filed: Nov. 11, 2010

(86) PCT No.: PCT/NL2010/050752
§ 371 (c)(1),
(2), (4) Date: Jul. 16, 2012

(87) PCT Pub. No.: WO2011/059326
PCT Pub. Date: May 19, 2011

(65) Prior Publication Data
US 2012/0276069 A1    Nov. 1, 2012

(30) Foreign Application Priority Data
Nov. 11, 2009 (EP) .................................... 09175723

(51) Int. Cl.
*A61K 31/721* (2006.01)
*A61K 31/727* (2006.01)
*A61K 47/48* (2006.01)
*A61L 27/38* (2006.01)
*A61L 27/52* (2006.01)

(52) U.S. Cl.
CPC ..... *A61K 47/48784* (2013.01); *A61K 47/48023* (2013.01); *A61L 27/3817* (2013.01); *A61L 27/3834* (2013.01); *A61L 27/52* (2013.01); *A61L 2400/06* (2013.01)

(58) Field of Classification Search
None
See application file for complete search history.

(56) References Cited

U.S. PATENT DOCUMENTS

2007/0149441 A1*  6/2007  Aeschlimann et al. ........... 514/8

FOREIGN PATENT DOCUMENTS

DE        4217916       12/1993
WO     2004063388        7/2004

OTHER PUBLICATIONS

Jin et al, Enzyme-mediated fast in situ formation of hydrogels from dextran-tyramine conjugates, 2007, Biomaterials 28: 2791-2800.*
Shinji Sakai, Yuko Ogushi, Koci Kawakami, "Enzymatically Crosslinked Carboxymethylcellulose-Tryamine Conjugate Hydrogel: Cellular Adhesiveness and Feasibility for Cell Sheet Technology," Science Direct, ActaBiomaterialia, Oct. 2008, 6 pages.
Motoichi Kurisawa, Joo Eun Chung, Yi Yan Yang, Shu Jun Gao and Hiroshi Uyama, "Injectable Biodegradable Hydrogels Composed of Hyaluronic Acid-Tyramine Conjugates for Drug Delivery and Tissue Engineering," ChemComm, Jun. 2005, 4 pages.
Aniq Darr and Anthony Calabro, "Synthesis and Characterization of Tyramine-Based Hyaluronan Hydrogels," J. Mater Sci: Mater Med (2009), 12 pages.
Rong Jin, Christine Hiemstra, Zhiyuan Zhong and Jan Fiejen, "Enzyme-Mediated Fast in Situ Formtion of Hydrogels from Dextran-Tyramine Conjugates," Science Direct, Biomaterials (2007), 10 pages.
Shinji Sakai, Keisuke Hirose, Kenichi Tagushi, Yuko Ogushi and Koei Kawakami, "An Injectable, in situ Enzymatically Gellable, Gelatin Derivative for Drug Delivery and Tissue Engineering," Biomaterials (2009), 7 pages.
R Jin, L.S. Moreira Teixeira, P.J. Dijkstra, M. Karperien, Z. Zhong, and J. Feijen, "Fast in-situ Formation of Dextran-Tyramine Hydrogels for In Vitro Chondrocyte Culturing," Abstracts, Journal of Controlled Release 132 (2008), 3 pages.

* cited by examiner

*Primary Examiner* — Layla Bland
(74) *Attorney, Agent, or Firm* — Tarolli, Sundheim, Covell & Tummino LLP

(57) ABSTRACT

The invention relates to composition comprising a dextran-tyramine conjugate and a conjugate selected from the group consisting of chondroitin sulphate-tyramine, collagen-tyramine, chitosan-tyramine, chitosan-phloretic acid, gelatine-tyramine, heparan sulphate-tyramine, keratin sulphate-tyramine, hyaluronic acid-tyramine and heparin-tyramine.

21 Claims, 12 Drawing Sheets

A

B

C

HYDROGELS BASED ON POLYMERS OF DEXTRAN TYRAMINE AND TYRAMINE CONJUGATES OF NATURAL POLYMERS

FIELD OF THE INVENTION

The invention is in the field of tissue engineering. More specifically, the invention is in the field of polymers which can be used in the preparation of hydrogels. More in particular, the invention relates to composition comprising a dextran-tyramine conjugate (Dex-TA) and a conjugate made of a glycosaminoglycan coupled to a tyramine or a collagen coupled to a tyramine, methods for producing them, and uses thereof

BACKGROUND OF THE INVENTION

Tissue engineering is a promising method for the regeneration of degenerated or lost cartilage. This approach generally involves the use of cells placed in three-dimensional scaffolds, the latter acting as a temporary artificial extracellular matrix (ECM). Injectable hydrogels may serve as temporary scaffolds to guide cell attachment and differentiation of chondrocytes and/or their progenitor cells, resulting in newly formed cartilage tissue. Compared to preformed hydrogels, injectable hydrogels have various advantages. They can be applied via a minimally invasive surgical procedure. They can fill irregular-shaped defects and allow easy incorporation of cells and bioactive molecules.

Therefore, in recent years injectable hydrogels have received much attention in cartilage tissue engineering. Several chemical crosslinking methods, such as photopolymerization, Schiff-base formation, and Michael-type addition reactions, have been employed to obtain injectable hydrogels that gel in situ. Recently, an efficient method, i.e. horseradish peroxidase (HRP)-mediated chemical crosslinking, has been developed to produce injectable hydrogels. Using this approach, Lee et al. reported on hyaluronic acid-based injectable hydrogels for protein release and Sakai et al. prepared gelatin-based injectable hydrogels in vitro and indicated their potential application in tissue engineering in vivo (Lee et al. Journal of Controlled Release, 2009, 134, 186-193; Sakai et al. Biomaterials, 2009, 30, 3371-3377). In Kurisawa et al. (Chem. Commun., 2005, 4312-4314) injectable biodegradable hydrogels composed of hyaluronic acid-tyramine conjugates for drug delivery and tissue engeneering are described. In Jin et at (Biomaterials 28 (2007), 2791-2800) hydrogels formed by enzymatic crosslinking of dextran-tyramine conjugates are described.

We previously showed that fast in situ forming injectable hydrogels can be obtained via enzymatic crosslinking of dextran-tyramine conjugates (Dex-TA) or chitosan-phloretic acid conjugates in the presence of HRP and hydrogen peroxide (Jin R. et al., Biomaterials. 2009 (13):2544-51 and Jin R. et al., Biomaterials, 2007 (18):2791-800.)

These hydrogels had good mechanical properties and low cytotoxicity. Chondrocytes incorporated in the gels remained viable and were capable of maintaining their phenotype and producing cartilaginous tissue. However, a disadvantage is that these gels have a low storage modulus. Increasing the storage modulus by increasing the polymer concentration results in hydrogels wherein chondrocytes change their chondrocytic phenotype rapidly. Therefore, it is an objective of the invention to provide a novel polymer suitable for forming biocompatible hydrogels, wherein chondrocytes maintain their phenotype. Furthermore, it is an objective of the invention to provide conjugates which can be used to prepare hydrogels which display better mechanical properties and/or are better broken down in a living animal.

SUMMARY OF THE INVENTION

The invention provides a composition comprising a dextran-tyramine conjugate and a conjugate selected from the group consisting of chondroitin sulphate-tyramine, collagen-tyramine, chitosan-tyramine, chitosan-phloretic acid, gelatine-tyramine, heparan sulphate-tyramine, keratin sulphate-tyramine, hyaluronic acid-tyramine and heparin-tyramine. Preferably, said composition comprises a heparin-tyramine (Hep-TA) conjugate and a dextran-tyramine conjugate (Dex-TA). In a preferred embodiment of said composition, Dex-TA and Hep-TA are present in a weight ratio between 95:5 and 5:95, more preferably between 75:25 and 25:75. Preferably, said composition further comprises a suitable amount of hydrogen peroxide and suitable amount of a peroxidase. Preferably, the amount of the tyramine conjugate comprising a tyramine moiety conjugated to a glycosaminoglycan or a collagen according to the invention, preferably a heparin-tyramine (Hep-TA) conjugate, in the composition is between 10 and 20 wt %, based on the weight of the composition. Preferably, the concentration of peroxidase in said composition is between 10-125 Units/ml (0.2 and 2.5 mg/ml). Preferably, the concentration of hydrogen peroxide is between 0.005 and 0.05 M. Preferably, said composition is in the form of an injectable hydrogel. Preferably, said composition further comprises a growth factor, preferably a Bone Morphogenetic Protein (BMP) or a Transforming Growth Factor beta (TGF-β).

In another aspect, the invention further provides a method of treating a subject comprising administering a composition according to the invention to a subject in need of such treatment.

In another aspect, the invention provides a kit comprising a dextran-tyramine conjugate and a conjugate selected from the group consisting of chondroitin sulphate-tyramine, collagen-tyramine, chitosan-tyramine, chitosan-phloretic acid, gelatine-tyramine, heparan sulphate-tyramine, keratin sulphate-tyramine, hyaluronic acid-tyramine and heparin-tyramine and optionally a peroxidase, hydrogen peroxide and/or an instruction for preparing an injectable hydrogel according to the invention.

In another aspect, the invention further provides a polymer of a heparin-tyramine (Hep-TA) conjugate and a dextran-tyramine conjugate (Dex-TA).

DESCRIPTION OF THE DRAWINGS

FIG. 16A shows that bovine chondrocytes, which were dynamically seeded using a spinner flask, can adhere and invade Dex-TA hydrogels by cell in-growth. The cells are stained purple by using the MTT assay, after 7 days in culture. FIG. 16B is a schematic representation of the assembly of a hydrogel construct consisting of a layer of Dex-TA with chondrocytes incorporated within and an adjacent layer of Dex-TA/Hep-TA 50/50 without cells. After 7 days in culture, cross-sections of the constructs were stained with toluidine blue, which stains heparin and DAPI, which stains nuclei, as shown in FIG. 13C. The arrows correspond to cell nuclei co-localizing with the heparin, indicating that cells have migrated from the Dex-TA to the Dex-TA/Hep-TA, which initially did not contain cells. This experiment indicates that Dex-TA/Hep-TA hydrogels can attract chondrocytes or progenitor cells, facilitate their in growth in the hydrogel construct and stimulate differentiation.

DETAILED DESCRIPTION OF THE INVENTION

Definitions

Figure 1A:
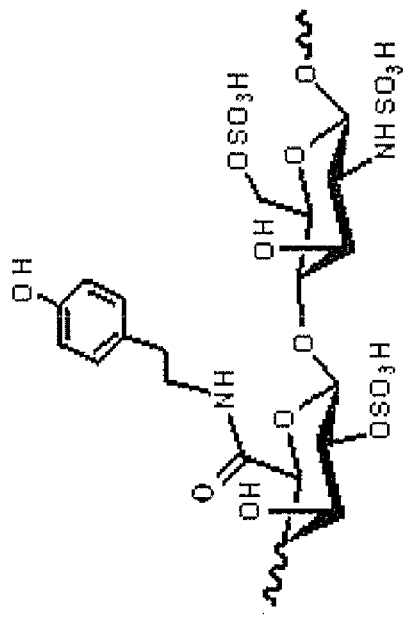
FIG. 1.(a) shows the synthesis of heparin-tyramine conjugates (Hep-TA).
FIG. 1(b) shows the hydrogel formation from dextran-tyramine (Dex-TA, black) and heparin-tyramine conjugates (Hep-TA, grey) via HRP-mediated crosslinking in the presence of $H_2O_2$.
Figure 1A:
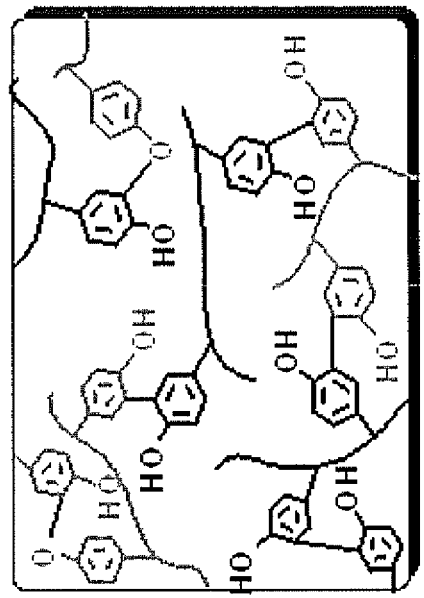
Figure 1B:
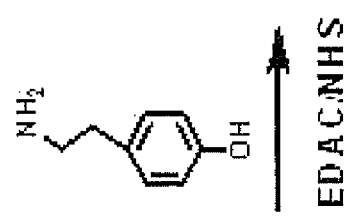
Figure 1B:
Figure 1B:
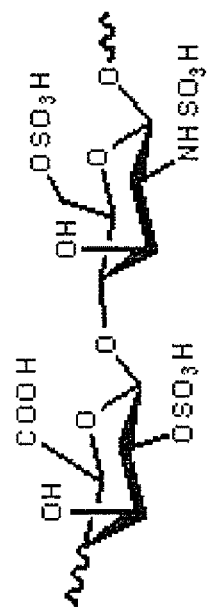
Figure 1B:
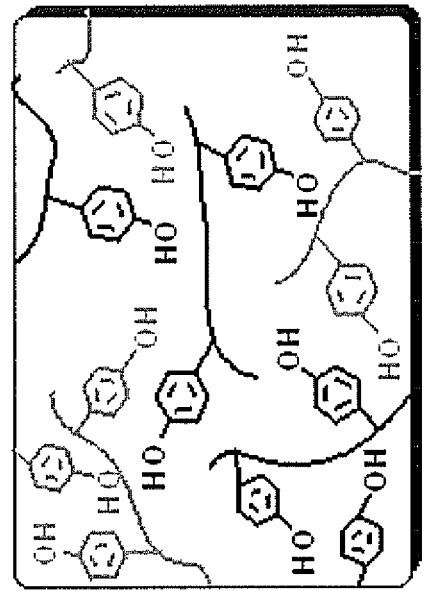

The term 'treatment of a patient in need of an implant' as used herein refers to a treatment aiming to restore or to replace the function of a missing tissue and wherein the provision of the hydrogel of the invention is aimed at improving regeneration of a damaged tissue wherein said implant is implanted. In other embodiments, the treatment is aimed at the sustained or extended release of a medicament or drug incorporated in said hydrogel. Preferably, said missing tissue is cartilaginous tissue. Preferably said sustained or extended release is a release which is at least 3, 4, 5, 6, 8, 10, 12 15, 20, 24 hours. In some embodiments said sustained or extended release is at least 1, 2, 3, 4, 5, 6, 7, 10, 14, 21 days. Preferably, said slow or sustained release is at least prolonged when compared to the same medicament not incorporated in a hydrogel of the invention, preferably by at least 3, 4, 5, 6, 8, 10, 12 15, 20, 24 hours. Preferably, said subject is suffering from a tissue defect, preferably a cartilage defect. Said subject is preferably a mammalian animal, preferably a human.

The term "hydrogel" as used herein refers to three-dimensional hydrophilic polymeric networks. Hydrogels have high water content, providing an environment similar to native cartilage. Besides, hydrogels allow for sufficient transportation of nutrients and waste products, which is essential for cell growth. Hydrogels can be categorized into preformed and injectable hydrogels. Hydrogels are preferably designed such that they will form in-situ and these systems are termed injectable hydrogels. They offer the advantages of good alignment with irregularly shaped defects and allow easy cell incorporation. Moreover, from the clinical point of view, implantation surgery can be avoided and replaced by a simple injection procedure.

The term "injectable hydrogel" refers to a solution which is capable of forming a hydrogel once it has been injected. Therefore, said solution is fluid enough to enable injection of said fluid.

The term "dextran-tyramine" as used herein refers to a dextran molecule grafted with tyramine molecules linked by a urethane bond or by an ester-containing diglycolic group. It is contemplated that also other groups having a free phenol coupled to dextran may be used.

The term "heparine-tyramine" as used herein refers to a heparin molecule grafted with tyramine molecules linked by a urethane bond or by an ester-containing diglycolic group. It is contemplated that also other molecules having a free phenol group coupled to heparin may be used.

The term "growth factor" as used herein refers to a molecule that elicits a biological response to improve tissue regeneration, tissue growth and organ function. Preferred growth factors are morphogens. The term 'morphogen' as used herein refers to a substance governing the pattern of tissue development and, preferably, the positions of the various specialized cell types within a tissue. Preferably, it spreads from a localized source and forms a concentration gradient across a developing tissue.

In preferred embodiments, a morphogen is a signalling molecule that acts directly on cells (preferably not through serial induction) to produce specific cellular responses dependent on morphogen concentration. Preferred morphogens include: a Decapentaplegic/Transforming growth factor beta (TGFbeta), Hedgehog/Sonic Hedgehog, Wingless/Wnt, an Epidermal growth factor (EGF), a Bone Morphogenic Protein (BMPs), and a Fibroblast growth factor (FGF). Preferably, said FGF comprises FGF2, KFG and FGF18. Preferably, said BMP comprises BMP2, BMP4, BMP6 and BMP7. Preferred TGFbeta's include TGFbeta1 and TGFbeta3. In some preferred embodiments, said growth factor comprises a protein of the extracellular matrix.

The term "growth factor antagonist" as used herein refers to secreted growth factor antagonists (BMP antagonists (noggin, gremlin), Wnt-antagonists (Dkk1, FrzB, sclerostin) and dual antagonists of both BMP and Wnt (Cerberus).

The term "homing" as used herein refers to a process wherein cells migrate to a target area (i.e. a tissue or a hydrogel) and settle in said area.

The term "tyramine conjugate" in aspects of the invention includes reference to conjugates comprising additional moieties conjugated to the primary conjugate. Examples thereof include hyaluronic acid conjugated to Hep-TA.

The term "suitable amount" with respect to peroxidase or peroxide as referred to herein, means a curing amount said substance, which refers to the ability to amount to gel formation in a composition of the invention. The gel formation may be established by the methods as referred to in the examples using the tilting method.

When reference is made herein to peroxide and peroxidase, these terms should be understood as referring to a curing system for crosslinking the tyramine conjugates in compositions of the invention. The skilled artisan will understand that alternative curing systems based on curing radicals, including oxygen radicals, may be used in aspects of the inventions and are envisioned as embodiments in aspects of the invention.

Description of the Embodiments

Composition of Hep-TA Conjugates and Dex-TA Conjugates

The present invention is based on the surprising finding that hydrogels comprising both Dex-TA and Hep-TA show significantly higher collagen production compared to Dex-TA hydrogels ($p<0.05$). Furthermore, it is based on the surprising finding that hydrogels comprising both Dex-TA and Hep-TA can attract significantly more cells from surrounding tissues and stimulate their ingrowth in the hydrogel compared to Dex-TA hydrogels ($p<0.05$). Without wishing to be bound by theory, it is believed that the higher collagen production may relate to the superior cell attracting properties of hydrogels comprising both Dex-TA and Hep-TA compared to Dex-TA hydrogels. This may be explained as follows:

The inventors have shown that the presence of Hep-TA in a hydrogels based on the composition according to the invention comprising Hep-TA/Dex-TA conjugates induces homing of cells which contribute to the recovery of damaged tissue, preferably cartilage tissue. Said cells are preferably chondrocytes, human mesenchymal stem cells and chondrogenic progenitor cells, which were all attracted to hydrogels made of said composition according to the invention, as shown in the example described herein. This demonstrates that Dex-TA/Hep-TA hydrogels are very suitable for use as a cell free hydrogel construct that can preferably be applied on a damaged cartilage surface. Said hydrogel can subsequently attract cells from the surrounding tissue, preferably cartilage, synovium, bone marrow or synovial fluid that can grow into the hydrogel and repair the damaged surface. Cells from the synovial fluid and/or bone marrow can migrate into said Dex-TA/Hep-TA hydrogel, allowing matrix to be produced within the hydrogel. In agreement to the induced cell attracting potential of Dex-TA/Hep-TA hydrogels, as assessed by a porous membrane assay, cell homing and ingrowth was also observed within the hydrogels. The inventors have shown that the chondrocytes are able to adhere and migrate into Dex-TA/Hep-TA hydrogels. Human mesenchymal stem cells and chondrogenic progenitor cells respond in a similar way. Taken together, the composition comprising Dex-TA/Hep-TA conjugates according to the invention are superior over compositions which do not comprise Hep-TA. It is believed that due to the cell attracting qualities of the hydrogels made of Dex-TA/Hep-TA conjugates, cells home to said hydrogels in greater numbers and infiltrate the hydrogels easy. It is believed that amongst other factors, the attraction of a greater number of collagen producing cells results in a higher collagen production, which is important for recovery of tissue damage. These effects can also be achieved when, instead of Hep-TA, another conjugate of a glycosaminoglycan coupled to a tyramine or a collagen coupled to a tyramine is used.

The invention therefore provides a composition comprising a dextran-tyramine conjugate and a conjugate selected from the group consisting of chondroitin sulphate-tyramine, collagen-tyramine, chitosan-tyramine, chitosan-phloretic acid, gelatine-tyramine, heparan sulphate-tyramine, keratin sulphate-tyramine, hyaluronic acid-tyramine and heparin-tyramine. Preferably, said composition comprises a heparin-tyramine (Hep-TA) conjugate and a dextran-tyramine conjugate (Dex-TA). Said compositions can be used to produce hydrogels that have superior characteristics compared to hydrogels having only Hep-Ta or Dex-TA as polymers. The incorporation of a conjugate selected from the group consisting of chondroitin sulphate-tyramine, collagen-tyramine, chitosan-tyramine, chitosan-phloretic acid, gelatine-tyramine, heparan sulphate-tyramine, keratin sulphate-tyramine, hyaluronic acid-tyramine and heparin-tyramine into hydrogels improves the in vitro and in vivo ability of chondrocytes present in the hydrogel to maintain a chondrocytic phenotype and to form cartilaginous tissue. Without wishing to be bound by theory, it is believed that the presence of the conjugate selected from the group consisting of chondroitin sulphate-tyramine, collagen-tyramine, chitosan-tyramine, chitosan-phloretic acid, gelatine-tyramine, heparan sulphate-tyramine, keratin sulphate-tyramine, hyaluronic acid-tyramine and heparin-tyramine promotes chondrocyte proliferation and differentiation as well as enhanced cartilage regeneration. A further advantage is that the presence of conjugates made of glycosaminoglycans or collagens and a tyramine greatly improves the biocompatibility of the hydrogel in vivo. Surprisingly, the biological properties of the glycosaminoglycans or collagens are not impaired by the coupling with a tyramine group. Furthermore, despite the reported steric hindrance or charge interactions, interactions of the acid groups in glycosaminoglycans and in particular heparin (e.g. $OSO_3$— and $NHSO_3$—) with the active site of the peroxidase enzyme, the inventors have shown that solutions with Hep-TA can form hydrogels within reasonably short gelation times. Another advantage is that hydrogels based on said compositions have a short degradation time. The collagen- or glycosaminoglycan-tyramines in aspects of the invention include conjugates between tyramine and chondroitin, collagen, chitosan, gelatine, heparan, keratin, hyaluroan and heparin.

Figure 10:
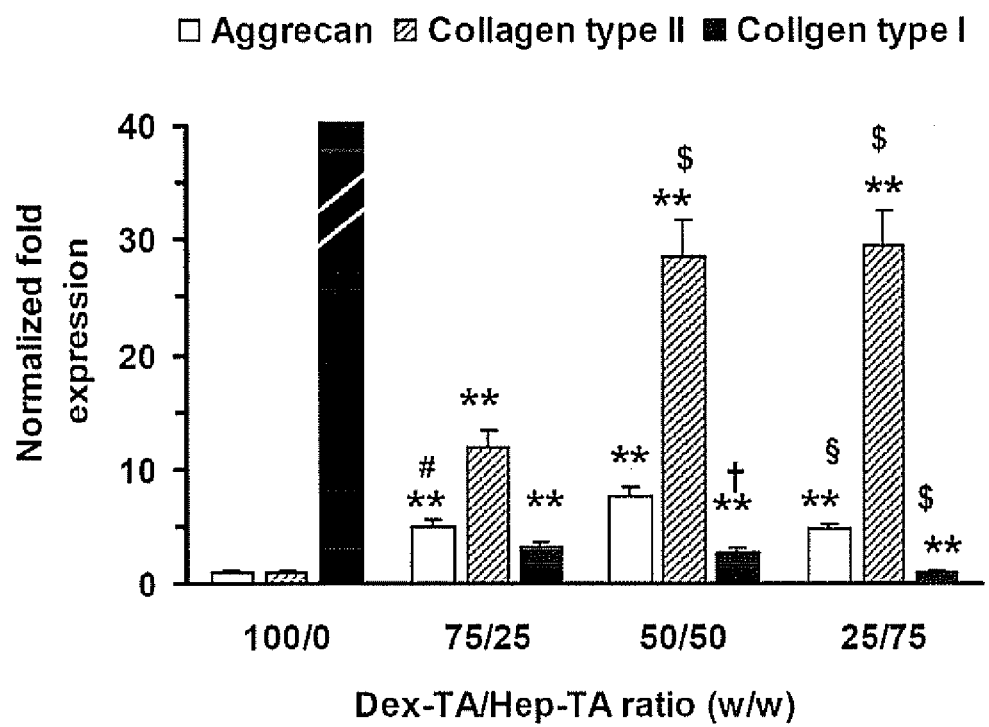
FIG. 10 shows a real-time PCR of cartilage specific markers (aggrecan and collagen type I & II) by incorporated chondrocytes in 20 wt % Dex-TA/Hep-TA hydrogels after 21 days in culture. The expressions of collagen type I & II and aggrecan were normalized to the expression of the housekeeping gene GAPDH. (**$p<0.01$ vs. 100/0 gel; #$p<0.05$ vs. 50/50 gel; §$p<0.01$ vs. 50/50 gel; \$ $p<0.01$ vs. 75/25 gel; † $p<0.05$ vs. 75/25 gel).

The inventors have performed experiments using hydrogels based on the composition according to the invention to determine the abilities of chondrocytes to maintain a chondrocytic phenotype and to form cartilaginous tissue in vitro. These abilities were evaluated after culturing in differentiation medium, up to 21 days by determining gene expression of collagen type I & II and aggrecan using RT-PCR. It is shown that the gene expression levels were dependent on the composition of the hydrogels (FIG. 10). The chondrocytes in Hep-TA hydrogels maintained significantly higher levels of aggrecan and type II collagen gene expressions compared to those in Dex-TA hydrogels, preferably at the same polymer concentration (p<0.001). In contrast, Dex-TA hydrogels expressed collagen transcripts mainly of type I instead of type II, suggesting a loss of chondrocyte phenotype. Additionally, the Hep-TA content in the hydrogels was found to up-regulate aggrecan and collagen type II mRNA levels in a content-dependent manner.

The heparin-tyramine conjugates are therefore advantageously used as a polymer in a composition for making a hydrogel. These advantages also apply to conjugates selected from the group consisting of chondroitin sulphate-tyramine, collagen-tyramine, chitosan-tyramine, chitosan-phloretic acid, gelatine-tyramine, heparan sulphate-tyramine, keratin sulphate-tyramine, hyaluronic acid-tyramine and heparin-tyramine. Medical application of the heparin-tyramine conjugates is therefore within the scope of the invention. This also applies to conjugates selected from the group consisting of chondroitin sulphate-tyramine, collagen-tyramine, chitosan-tyramine, chitosan-phloretic acid, gelatine-tyramine, heparan sulphate-tyramine, keratin sulphate-tyramine, hyaluronic acid-tyramine and heparin-tyramine. More specifically, the medical use of these conjugates in the field of tissue engineering belongs to the scope of the invention. Other polymers may be used in combination with conjugates selected from the group consisting of chondroitin sulphate-tyramine, collagen-tyramine, chitosan-tyramine, chitosan-phloretic acid, gelatine-tyramine, heparan sulphate-tyramine, keratin sulphate-tyramine, hyaluronic acid-tyramine and heparin-tyramine. Preferred polymers comprise polymers based on natural polymers, preferably glycosaminoglycans or polymers present in cartilage tissue. Preferred natural polymers comprise phenol conjugated chitosans, collagen, gelatin, chondroitin sulphate, heparan sulphate, keratin sulphate or hyaluronic acid. Especially preferred are polymers which are coupled to a tyramine, phloretic acid or tyrosine moiety. Preferably, the weight ratio between a conjugate selected from the group consisting of chondroitin sulphate-tyramine, collagen-tyramine, chitosan-tyramine, chitosan-phloretic acid, gelatine-tyramine, heparan sulphate-tyramine, keratin sulphate-tyramine, hyaluronic acid-tyramine and heparin-tyramine and other polymers is higher than 10/90, more preferably higher than 15/85, 20/80, 25/75.

Heparin-tyramine (Hep-TA) conjugates are known from WO2004063388 and DE 4217916. Conjugates selected from the group consisting of chondroitin sulphate-tyramine, collagen-tyramine, chitosan-tyramine, chitosan-phloretic acid, gelatine-tyramine, heparan sulphate-tyramine, keratin sulphate-tyramine, hyaluronic acid-tyramine and heparin-tyraminecan be synthesized by the coupling reaction of the amino group of tyramine to the carboxylic acid groups of heparin using for example EDC/NHS activation (A Darr and A Calabro Journal of Materials Science: Materials in Medicine 2009; 20: 33-44). Preferably, heparin with a molecular weight between 5 kD and 25 kD, most preferably 10 kD is used. In some embodiments, said Hep-TA conjugates have a degree of substitution of tyramine residues between 10 and 20, defined as the number of tyramine moieties per 100 repeating disaccharide units of heparin, as determined by a UV measurement. More preferably, said degree of substitution is between 13 and 17 and even more preferably between 14 and 16 and most preferably 15. Conjugates with said degree of substitution are optimal for preparing hydrogels wherein cells are incorporated. In other embodiments, the degree of substitution is between15-25. Conjugates with degree of substitution between 15-25 are optimal for preparing hydrogels wherein pharmaceutically active compounds are incorporated, as such hydrogels display very suitable release profiles. Any heparin molecule can be used, but clinical grade heparin is preferred. In a typical procedure, heparin sodium is dissolved in 4-morpholino ethanesulfonic acid (MES), to which N-ethyl-N'-(3-dimethylaminopropyl)carbodiimide hydrochloride (EDAC) and N-hydroxysuccinimide (NHS) are added. After half an hour a dimethylformamide (DMF) solution containing tyramine is added and the mixture is stirred under nitrogen. After a few days, the obtained mixture is neutralized with NaOH and ultrafiltrated, first with NaCl and then deionized water. The resultant Hep-TA conjugate can then be obtained in the form of a foam after freeze-drying.

Dextran-TA conjugates are known in the art (R Jin et al. Journal of Controlled Release 2008; 132: e24-e6). Preferred dextran-tyramine conjugates have a degree of substitution, defined as the number of tyramine units per 100 anhydroglucose rings in dextran, of between 10 and 20, more preferably between 12 and 18, more preferably between 13-17, 14-18 and most preferably 15.

Figure 2:
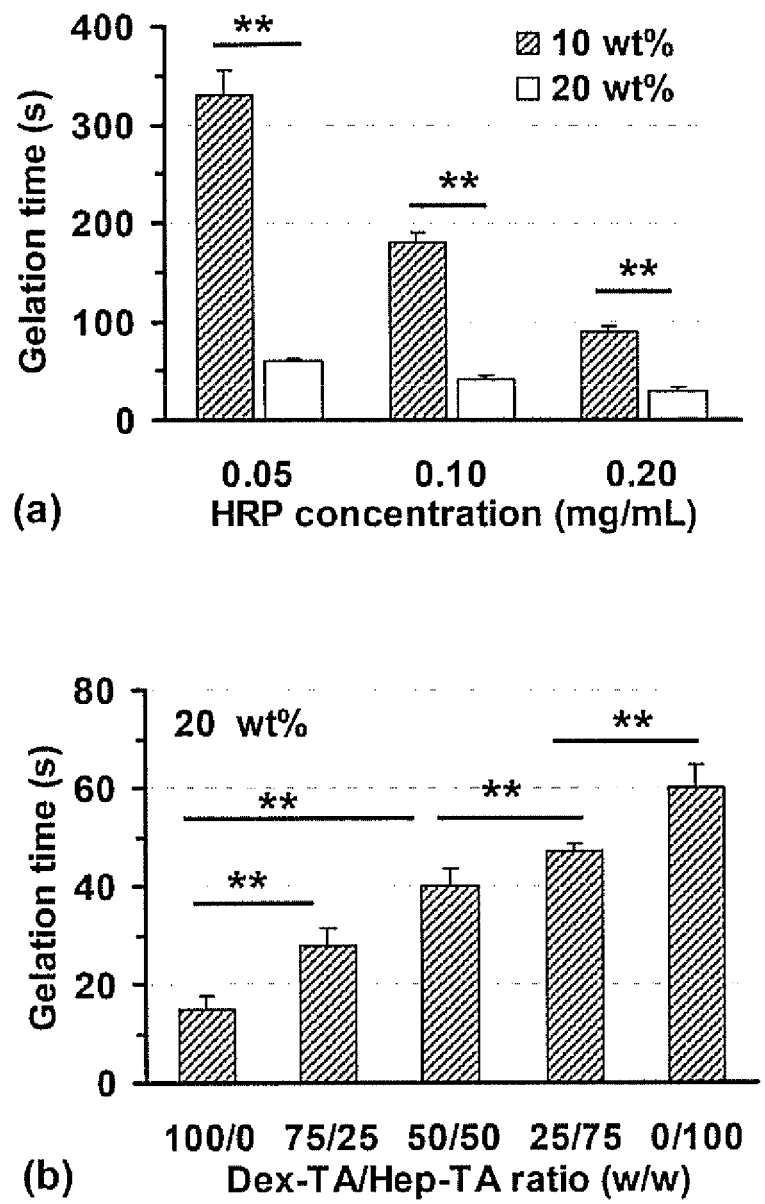
FIG. 2(a) shows the gelation times of Hep-TA hydrogels (10 and 20 wt %) as a function of HRP concentration. The molar ratio of $H_2O_2$/TA was kept at 0.2. (b) Gelation times of Hep-TA/Dex-TA hydrogels (20 wt %) as a function of Hep-TA/Dex-TA ratio (w/w). The concentrations of HRP and $H_2O_2$ were kept at 15 Units/mL and 0.01 M, respectively. (**p<0.01)

An advantage of the addition of Dex-TA conjugates is that the hydrogel swelling properties are improved. In addition, gelation time of hydrogels based on said composition is shorter (FIG. 2a). Furthermore, addition of Dex-TA to hydrogels based on conjugates selected from the group consisting of chondroitin sulphate-tyramine, collagen-tyramine, chitosan-tyramine, chitosan-phloretic acid, gelatine-tyramine, heparan sulphate-tyramine, keratin sulphate-tyramine, hyaluronic acid-tyramine and heparin-tyramine results in stronger gels. Preferably, the molecular weight (MW) of dextran is between 10 and 80 kD, more preferably between 5 and 80 kD.

In some embodiments, the molecular weight (MW) of dextran in said Dex-TA is between 10-20 kD, preferably around 14 kD, to prepare hydrogels. Even more preferred is a composition according to the invention for the preparation of a said hydrogel, wherein the degree of substitution of tyramine units in Dex-TA is between 5 and 20, and more preferably between 10-15. An advantage of said hydrogels is that they have excellent characteristics for supporting cells.

In other preferred embodiment of said composition, said dextran has a molecular weight between 20-40 kD, preferably around 31 kD. It is even more preferred if the degree of substitution of tyramine in Dex-TA is in between 10-25. An advantage is that said hydrogels are stronger and have a molecular structure which is very suitable for storing molecules, such as medicaments, growth factors or growth factor antagonists, which are slowly released by the hydrogel.

Figure 14:
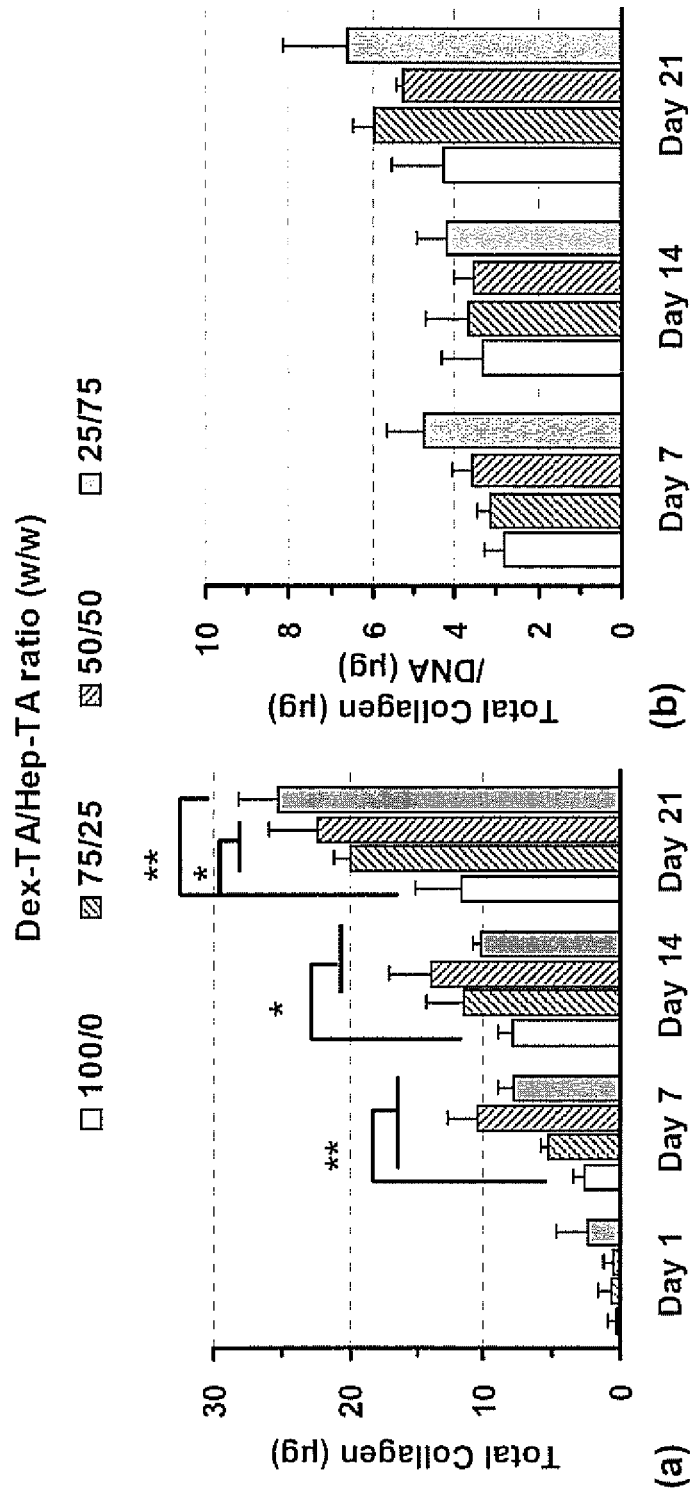
FIG. 14.(a) shows the total collagen and (b) total collagen normalized to DNA content in Dex-TA/Hep-TA hydrogels containing chondrocytes after in vitro culturing for 1, 7, 14 and 21 days. Cell seeding density: $5\times10^6$ cells/mL. (*$p<0.05$, **$p<0.01$).

Effect of Weight Ratio of Dex-TA/Hep-TA on Gene Expression and Collagen Production The inventors have also shown that the weight ratio of Dex-TA/Hep-TA in a hydrogel has an effect on gene expression and collagen production of cells in a hydrogel. For, example, it was observed that the highest collagen production was obtained in hydrogels from the 50/50 and 25/75 Dex-TA/Hep-TA hydrogel. Therefore, in some embodiments a weight ratio of Dex-TA/Hep-TA between 50/50 and 25/75 is preferred. This is consistent with the results for collagen type II staining and the RT-PCR findings for collagen type II gene expression. The total collagen accumulation increased in time and reached the highest value at day 21 at all compositions (FIG. 14a). When normalized to the DNA content, the total collagen content was statistically similar in all five systems at each time point (FIG. 14b).

It was further observed that aggrecan gene expression was maximized when the Dex-TA/Hep-TA weight ratio was 50/50 while collagen type II gene expression was highest for hydrogels with Dex-TA/Hep-TA weight ratio of 50/50 and 25/75. Toluidine blue was used to stain deposited proteoglycans by chondrocytes in Dex-TA/Hep-TA hydrogels cultured for 21 days. Proteoglycans stained purple/blue were observed in Dex-TA hydrogels. Unfortunately, in Dex-TA/Hep-TA hydrogels, due to the presence of heparin, which is stained positive using toluidine blue, the entire gels showed intense background staining. Thus, immunofluorescence staining of chondroitin sulfate and collagen type II was used to detect accumulation of newly formed cartilaginous matrix.

Figure 12:
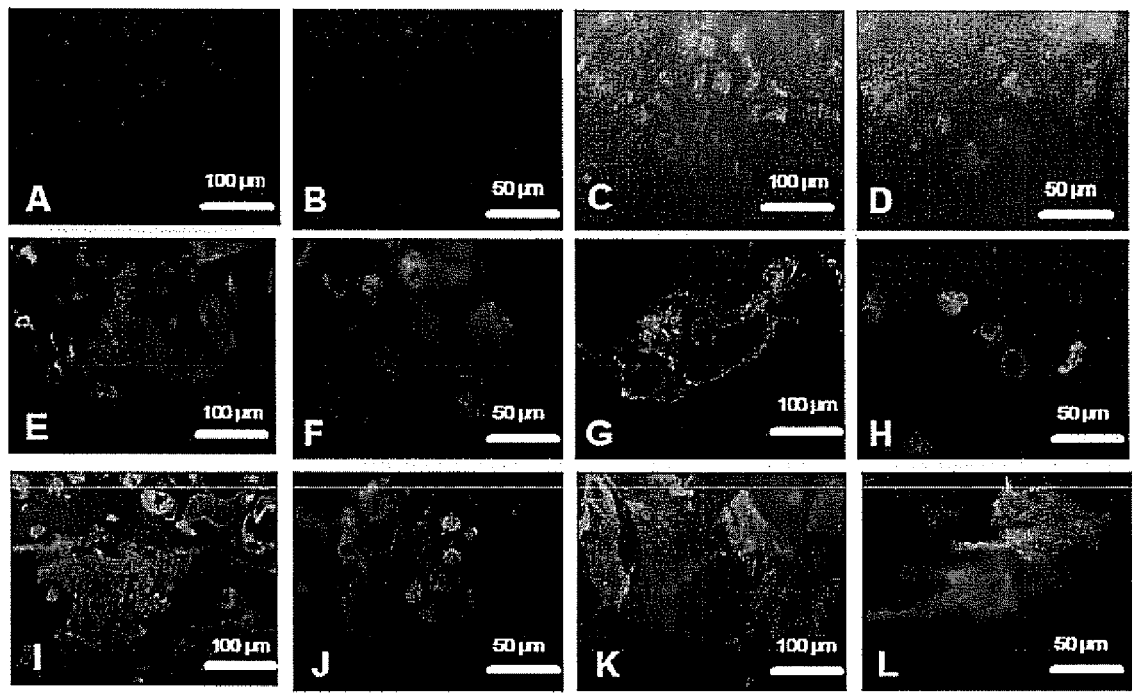
FIG. 12 shows a chondroitin sulfate immunofluorescent staining of the Dex-TA/Hep-TA hydrogels containing chondrocytes after in vitro culturing for 21 days. Different Dex-TA/Hep-TA ratios: 100/0 (E and F), 75/25 (G and H), 50/50 (I and J) and 25/75 (K and L). The section of bovine cartilage without or with incubation with primary antibodies was used as a negative (A and B) and positive (C and D) control, respectively.
Figure 13:
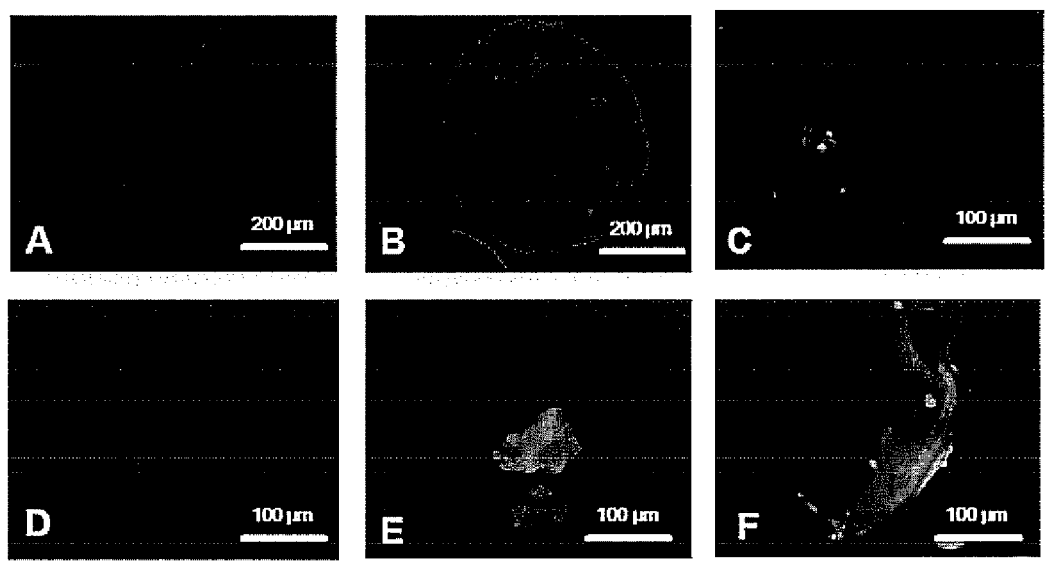
FIG. 13 shows a collagen type II immunofluorescent staining of the Dex-TA/Hep-TA hydrogels containing chondrocytes after in vitro culturing for 21 days. Different Dex-TA/Hep-TA ratios: 100/0 (C), 75/25 (D), 50/50 (E) and 25/75 (F). The section of pellet human chondrocytes at 21 days without or with incubation with primary antibodies was used as a negative (A) and positive (B) control, respectively.

The results confirmed the production of cartilaginous matrix in Dex-TA/Hep-TA hydrogels (FIGS. 12 and 13). The 50/50 and 25/75 Dex-TA/Hep-TA hydrogels showed a more intense staining of chondroitin sulfate and collagen type II than the 100/0 and 75/25 gels. In addition, the chondroitin sulfate in 100/0 and 75/25 hydrogels was present only in the pericellular region, while in 50/50 and 25/75 hydrogels, the chondroitin sulfate was evenly distributed over the pericellular and extracellular region. Since the 50/50 and 25/75 Dex-TA/Hep-TA hydrogels showed a degree of swelling of 16, statistically higher than 100/0 and 75/25 gels (9 and 13, respectively) (FIGS. 8), 50/50 and 25/75 hydrogels may induce more facilitated proteoglycan diffusion into the extracellular regions, thereby resulting in a more even distribution.

Figure 7:
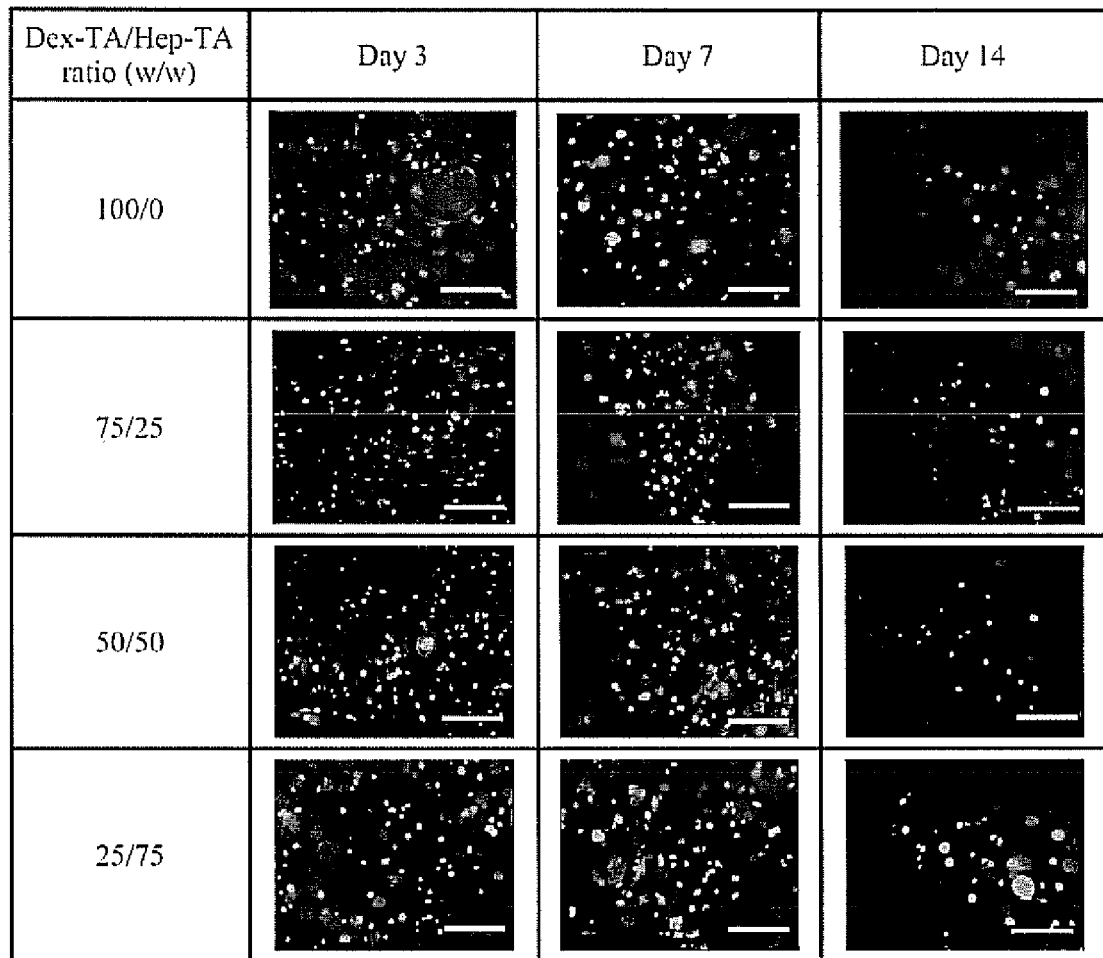
FIG. 7 shows the live-dead assay showing the chondrocytes incorporated in Dex-TA/Hep-TA hydrogels after 3, 7 and 14 days in culture. Cell density is $5\times10^6$ cells/mL gel. Scale bar: 200 μm.
Figure 8:
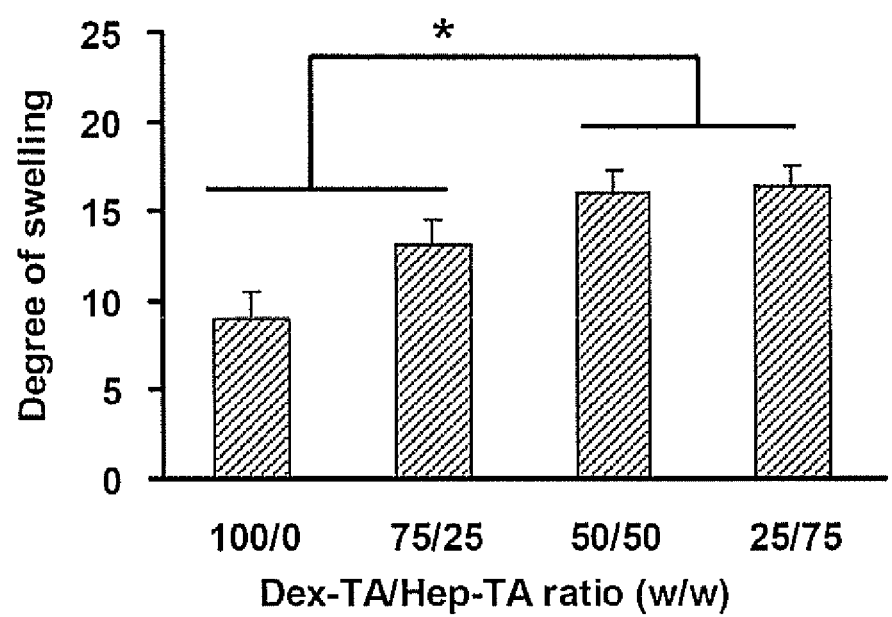
FIG. 8 shows the degree of swelling of 20 wt % Dex-TA/Hep-TA hydrogels containing chondrocytes after incubating for 3 days in vitro. Cell seeding density: $5\times10^6$ cells/mL. (*$p<0.05$).
Figure 9:
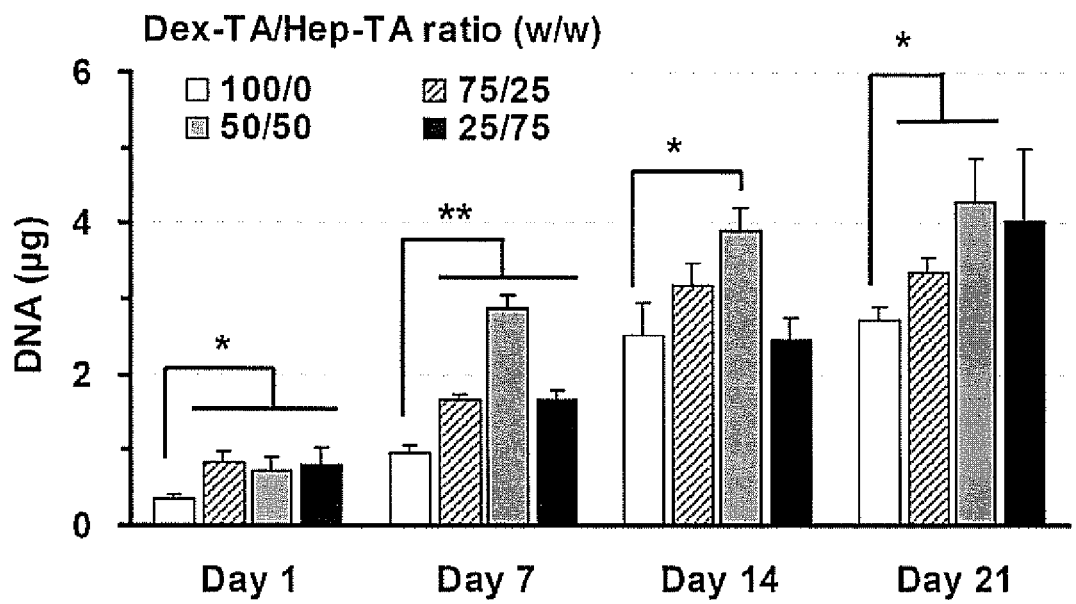
FIG. 9 shows the DNA content of 20 wt % Dex-TA/Hep-TA hydrogels containing chondrocytes after in vitro culturing for 1, 7, 14 and 21 days. Cell seeding density: $5\times10^6$ cells/mL. (*$p<0.05$, **$p<0.01$).

Effect of Weight Ratio of Dex-TA/Hep-TA on Viability and Proliferation of Cells in the Hydrogel Dex-TA and Dex-TA/Hep-TA hydrogels at Dex-TA/Hep-TA weight ratios of 100/0, 72/25, 50/50 and 25/75 were chosen for the biological studies due to their shorter gelation time and higher storage modulus compared to Hep-TA hydrogels. The biocompatibility of 20 wt % hydrogels was analyzed by a Live-dead assay after culturing for 3, 7 and 14 days, in which live cells fluoresce green and dead cells fluoresce red. At day 3, about 10-15% dead cells were present in the Dex-TA hydrogels, while over 95% chondrocytes remained viable in the Dex-TA/Hep-TA and Hep-TA hydrogels (FIG. 7). The compromised cell viability observed for the Dex-TA hydrogel may be attributed to the high crosslinking density of the hydrogels, and/or a limited nutrients supply resulting from the low degree of swelling in medium (FIG. 8). A CyQuant DNA assay was used to determine the viability and proliferation of chondrocytes inside the Dex-TA/Hep-TA hydrogels up to 21 days (FIG. 9). In general, the DNA content increased in time for the hydrogels at different Dex-TA/Hep-TA ratios from 100/0 to 25/75, indicative of cell proliferation. The chondrocytes in the hydrogels containing both Dex-TA and Hep-TA conjugates proliferated better than in Dex-TA hydrogels at all time intervals. This can be ascribed to both the enhancement of nutrient exchange in these highly swollen hydrogels and the potential biological role of heparin on the chondrocytes. The 50/50 Dex-TA/Hep-TA hydrogel revealed the best proliferation of chondrocytes compared to the others (25/75 and 75125), which suggested that there exists an optimal Dex-TA/Hep-TA ratio for cell proliferation. Therefore, in some embodiments, a Dex-TA/Hep-TA weight ratio between 45/55 and 55/45 is preferred, more preferably a ratio of substantially 50/50.

Effect of Weight Ratio of Dex-TA/Hep-TA on Gelation Time

The weight ratio of Dex-TA/Hop-TA has also an effect on the gelation time in hydrogels prepared with a composition comprising Dex-TA/Hep-TA conjugates. Gelation time of hydrogels can be monitored at 37° C. by the vial tilting method. The gelation times as a function of Dex-TA/Hep-TA weight ratio are presented in FIG. 2b. Generally, increasing the amount of De-TA conjugates decreased the gelation time of the hydrogel. When the Dex-TA/Hep-TA ratio decreased from 75/25 to 25/75, the gelation times slightly increased from 30 to 50 s.

Effect of Weight Ratio of Dex-TA/Hep-TA on Swelling Ratio

Increasing the Hep-TA content in Hep-TA in Dex-TA/Hep-TA hydrogels also showed an increase in the swelling ratio of the hydrogel (p<0.05). This high swelling ratio is believed to be due to the low crosslinking density or due to the electrostatic repulsive force between negatively-charged carboxylic acid and sulfate groups in the heparin at the physiological pH of 7.4. Therefore, in preferred embodiments, the weight ratio of Dex-TA/Hep-TA is higher than 25/75, more preferably 30/70, 35/65, 40/60, 45/55, 50/50, 55/45, 60/40, 65/35, 70/30, 75/25.

Effect of Weight Ratio of Dex-TA/Hep-TA on Storage Modulus

Figure 5:
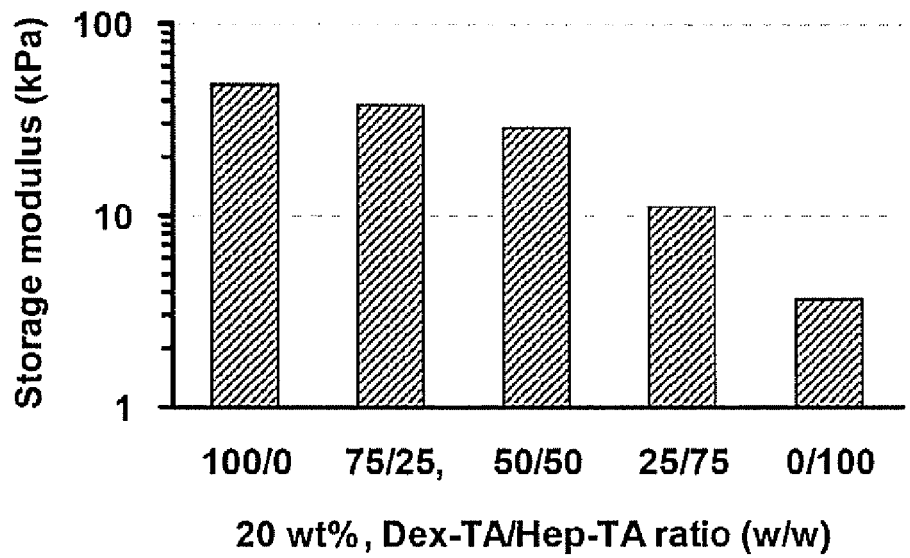
FIG. 5 shows storage moduli of Dex-TA/Hep-TA hydrogels. The concentrations of HRP and $H_2O_2$ were kept at 15 Units/mL and 0.01 M, respectively.
Figure 6:
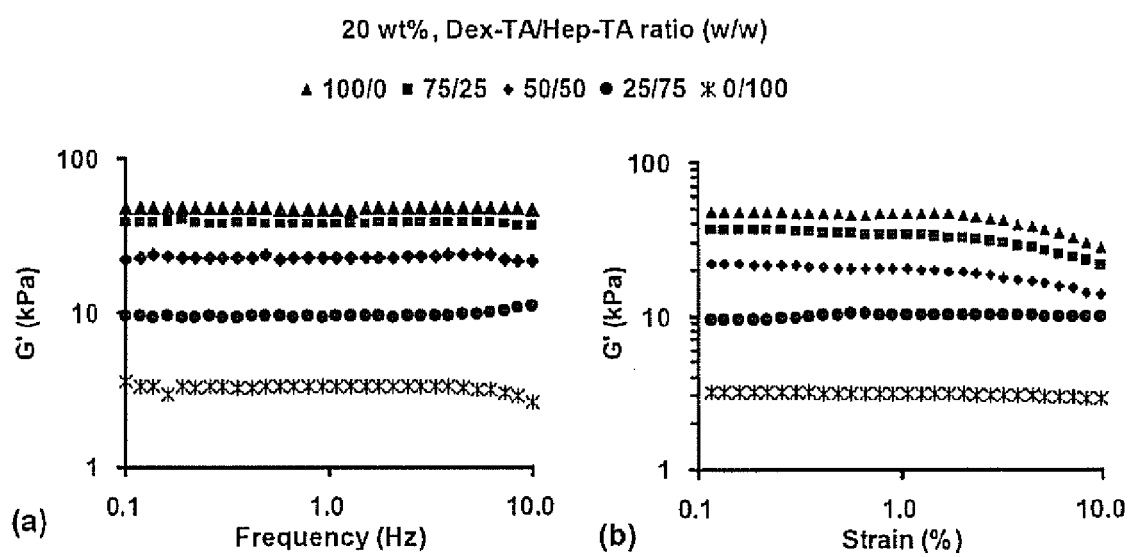
FIG. 6(a) shows the frequency sweep and (b) strain sweep of Dex-TA/Hep-TA hydrogels.

Varying the Dex-TA/Hep-TA weight ratio has also influence on the rheological properties of a hydrogel prepared therewith. Rheological measurements were performed to study the influence of the Hep-TA content on the mechanical properties of the hydrogels. The hydrogel prepared from Hep-TA at a concentration of 80 wt % and 20% Dex-TA showed a low storage modulus (G') of 3.6 kPa. The storage modulus of the Dex-TA/Hep-TA hydrogels increased from 3.6 to 48 kPa with decreasing Hep-TA content in the gels (FIG. 5). This indicated combination of Dex-TA and Hep-TA could overcome the disadvantage on the relatively low modulus of Hep-TA gels. The frequency and strain sweeps Dex-TA/Hep-TA hydrogels are presented in FIG. 6. From the frequency sweep experiments it is found that the hydrogels are elastic and the storage modulus is not dependent on the frequency (FIG. 6a). From the strain sweep tests, the properties of the hydrogels with a high Dex-TA/Hep-TA weight ratio (50/50 or 100/0) were strain independent within a strain range of 0.1-1% (FIG. 6b). As the strain increased to 2% or even higher values, the storage moduli decreased, indicating a breakdown of the network. However, the moduli of the hydrogels with a Dex-TA/Hep-TA weight ratio of 25/75 and 100/0 appeared independent of the strain up to 10%, suggesting a more robust nature of these hydrogels. Therefore, for some embodiments, a Dex-TA/Hep-TA weight ratio between 25/75 and 100/0 is preferred. However, to maintain the chondrocyte phenotype, it is essential to include Hep-TA in said composition. Therefore, the Dex-TA/Hep-TA weight ratio in said composition is preferably at least 99/1, more preferably, 98/2, 97/3, 96/4, 95/5, 94/6, 93/7, 92/8, 91/9, 90/10, 85/15, 80/20, 75/25.

Hydrogel

In another aspect, the invention relates to a composition according to the invention with a suitable amount of hydrogen peroxide and suitable amount of a peroxidase a hydrogel comprising a solution the heparin-tyramine (Hep-TA) conjugate according to the invention. Any peroxidase can be used, but horse radish peroxidase (HRP) is preferred. The, enzyme-mediated crosslinking of phenol moieties in the presence of HRP and $H_2O_2$, a method which is used to form tyramine conjugated dextrans and phloretic acid conjugated chitosans (R Jin et Biomaterials 2007; 28: 2791-800; R Jin et al. Biomaterials 2009; 30: 2544-51), is applied to form hydrogels from the Hep-TA conjugates, preferably at polymer concentrations of 10 and 20 wt %.

Preferably, the concentration of peroxidase is between 10-125 Units/ml. It was found that, by increasing the HRP concentration from 15-60 Units/ml, the gelation time decreased from about 340 s to 30 s ($p<0.05$).

The amount of the heparin-tyramine (Hep-TA) conjugate or the composition preferably is present at a concentration between 10 and 20 wt %. Shorter gelation times (less than 60 s) were observed for the 20 wt % hydrogels than for 10 wt % hydrogels, which can be explained by the presence of more crosslinkable moieties in the 20 wt % hydrogels.

At concentrations of HRP of 15 Units/ml and concentrations of $H_2O_2$ of 0.01 M, biocompatible hydrogel/cell constructs were obtained. Therefore, said concentration of hydrogen peroxide comprises preferably between 0.005 and 0.05 M.

These concentration ranges are preferably also applied in the preparation of the hydrogels of Hep-TA, Dex-TA and mixtures thereof.

In a preferred embodiment, said composition further comprises cells, preferably stem cells and or chondrocytes, wherein said stem cells are more preferably mesenchymal stem cells, embryonic stem cells or pluripotent stem cells or a combination of different stem cells.

In another preferred embodiment, said composition further comprises a growth factor, preferably a Bone Morphogenetic Protein or a TGFbeta. An advantage thereof is that growth factors accelerate differentiation and migration of relevant cells in the implant or in the surrounding tissue and said use increases the successful regeneration, reconstruction and replacement of lost and worn out tissues. Without wishing to be bound by theory, it is believed that as a result of the presence of said growth factor, the balance between factors that stimulate and factors that inhibit cell proliferation, cell differentiation, cell maturation, cell death and the formation of a functional organ cell growth is altered such that a better regeneration is achieved. In another embodiment, said hydrogel comprises a therapeutically effective medicament. Said medicament may be any pharmaceutically effective compound or biological molecule, including but not limited to a small molecule, a hormone, a growth factor, a growth factor antagonist, an anti-cancer drug.

In a preferred embodiment, said hydrogel is an injectable hydrogel. The hydrogels according to the invention can also be marketed as pre-filled syringes.

Hydrogel samples of Hep-TA or Hep-TA/Dex-TA mixtures at polymer concentrations of 10 or 20 wt % can be prepared in vials preferably at 37° C. In a typical procedure, a preferably freshly prepared solution of $H_2O_2$ (preferably in PBS) and peroxidase is added to a PBS solution of said Hep-TA or said composition and the mixture is gently mixed. The time to form a gel (denoted as gelation time) can be determined using the vial tilting method. Preferably, no flow within 1 min upon inverting the vial is regarded as the gel state.

A skilled person can prepare a hydrogel with a Hep-TA conjugate according to the invention or a composition according to the invention, to obtain a hydrogel having the optimal strength by optimizing the HRP concentration and/or the Dex/TA/Hep-TA weight ration (see FIG. 2a).

In another aspect, the invention further provides a method of treating a subject in need of tissue repair by providing a composition or hydrogel according to the invention. Said composition or hydrogel may be used in a mono-therapy (i.e. use of the hydrogel, composition alone). Alternatively, the composition or hydrogel according to the invention may be used as an adjunct, or in combination with other known therapies.

Preferably, the composition or hydrogel according to the invention may be administered by injection into an area where an implant is required for replacing a tissue. In another embodiment, said composition or hydrogel is administered to a tissue where sustained release of a medicament is required. Preferably said hydrogel is formed in situ in said area. Preferably, said hydrogel is formed within 2 hours, more preferably within 90, 80, 70, 60, 50, 40, 30, 20, 10, 9, 8, 7, 6, 5, 4, 3, 2, 1 minute(s). In some embodiments, said injection may be intravenous (bolus or infusion) or subcutaneous (bolus or infusion).), for example for closing a vessel.

In some embodiments, cells (such as chondrocytes, fibroblasts, osteoblasts, osteoclasts, mesenchymal stem cells, stem cells (not from human embryos) or a biopt and other cells as described herein etc.), medicaments, growth factors, scaffolds or other factors as described herein are provided separately from said composition or hydrogel according to the invention or mixed therewith in situ. In a preferred embodiment, said composition or hydrogel is administered intratumorally. More preferably, said hydrogel formed in the tumor contains an antitumor medicament, including but not limited to IL-2.

It will be appreciated that the amount of composition or hydrogel according to the invention required will be determined by for example the volume of said area where a tissue is to be replaced, but in addition to the swelling behaviour and degradation characteristics of said hydrogel and whether the composition or hydrogel is being used as a monotherapy or in a combined therapy. If said treatment is also used to provide slow release of a medicament, then the amount is also dependent on de dose of a medicament incorporated in said hydrogel and the pharmacokinetics of said medicament.

Optimal dosages to be administered may be determined by those skilled in the art, and will vary with the particular medicament in use, the strength of the preparation, the mode of administration, and the advancement of the disease condition. Additional factors depending on the particular subject being treated will result in a need to adjust dosages, including subject age, weight, gender, diet, and time of administration.

Known procedures, such as those conventionally employed by the pharmaceutical industry (e.g. in vivo experimentation, clinical trials, etc.), may be used to establish specific formulations of the medicament according to the invention, and precise therapeutic regimes (such as daily doses and the frequency of administration).

For slow release application, generally a daily dose of between 0.01 pg/kg of body weight and 1.0 g/kg of body weight of the hydrogel according to the invention may be used for the prevention and/or treatment of the specific medical condition. More preferably, the daily dose is between 0.01 mg/kg of body weight and 100 mg/kg of body weight. Daily doses may be given as a single administration. Alternatively, the medicament may require administration twice or more times during a day.

As an example, the medicament according to the invention may be administered as two (or more depending upon the severity of the condition) daily doses of between 25 mg and 5000 mg. A patient receiving treatment may take a first dose upon waking and then a second dose in the evening (if on a two dose regime) or at 3 or 4 hourly intervals thereafter. Alternatively, a slow release device may be used to provide optimal doses to a patient without the need to administer repeated doses.

In some embodiments, especially wherein said medicament is a peptide or a protein, administration is preferably less frequent, ranging from twice a week up to once per three months or even more preferably a single dosis. Some embodiments, said administration is once a week, once every two week, once every three weeks, once per month, once per two months.

The invention is now illustrated in a non-limiting manner by the following examples.

TABLE 1

Polymerase Chain Reaction Primers

| Primer | Direction | Sequence | Annealing Temp (° C.) |
|---|---|---|---|
| Bovine aggreean | Forward | 5' GACCAGAAGCTGTGCGAGGA 3' | 60 |
|  | Reverse | 5' GCCAGATCATCACCACACAG 3' |  |
| Bovine collagen, type IIa1 | Forward | 5' ATCAACGGTGGCTTCCACT 3' | 60 |
|  | Reverse | 5' TTCGTGCAGCCATCCTTCAG 3' |  |
| Bovine collagen, type Ia1 | Forward | 5' GCGGCTACGACTTGAGCTTC 3' | 60 |
|  | Reverse | 5' CACGGTCACGGACCACATTG 3' |  |
| Bovine GAPDH | Forward | 5' GCCATCACTGCCACCCAGAA 3' | 60 |
|  | Reverse | 5' GCGGCAGGTCAGATCCACAA 3' |  |

EXAMPLES

Materials

Heparin sodium (from porcine intestinal mucosa) was purchased from Celsus (MW 3000-30000), Inc. N-ethyl-N'-(3-dimethylaminopropyl)carbodiimide hydrochloride (EDAC) was purchased from Fluka. Tyramine (TA), hydrogen peroxide ($H_2O_2$), 4-morpholino ethanesulfonic acid (MES) and N-hydroxysuccinimide (NHS) were obtained from Aldrich-Sigma. Horseradish peroxidase (HRP, type VI, ~300 purpurogallin unit/mg solid) was purchased from Aldrich and used without further purification. All other solvents were used as received. Dextran-tyramine (denoted as Dex-TA) conjugates with a degree of substitution, defined as the number of tyramine units per 100 anhydroglucose rings in dextran, of 15 were prepared as previously reported (R Jin et al. Journal of Controlled Release 2008; 132: e24-e6.).

Synthesis and Characterization of Heparin-Tyramine Conjugate

A heparin-tyramine conjugate (denoted as Hep-TA) was synthesized by the coupling reaction of tyramine amine groups to heparin carboxylic acid groups using EDAC/NHS activation. In a typical procedure, heparin sodium (2.0 g) was dissolved in 20 of MES (0.1 M, pH 6.0), to which EDAC (288 mg, 1.5 mmol) and NHS (227 mg, 1.5 mmol) were added. After 30 min, 6 mL of a DMF solution 5 containing tyramine (69 mg, 0.5 mmol) was added and the mixture was stirred under nitrogen. After 3 days, the mixture was neutralized with 1 M NaOH and ultrafiltrated (MWCO 1000), first with 50 mM NaCl and then deionized water. The resultant Hep-TA conjugate was obtained in the form of a foam after freeze-drying (yield: 1.9 g, 95%). The degree of substitution of tyramine residues in the Hep-TA conjugate, defined as the number of tyramine moieties per 100 repeating disaccharide units of heparin, was 15, as determined by a UV measurement (A Darr and A Calabro Journal of Materials Science: Materials in Medicine 2009; 20: 33-44).

In brief, the Hep-TA conjugate was dissolved in PBS at a concentration of 2 mg/mL and the absorbance at 275 nm was measured using a Cary 300 Bio ultraviolet/visible spectrophotometer (Varian). An unmodified heparin solution (2 mg/ml) was used as a blank. The absorbance was correlated to the concentration of tyramine in the conjugate using a calibration curve obtained from tyramine solutions in PBS.

Hydrogel Formation and Gelation Time

Hydrogel samples (~0.25 mL) of Hep-TA or Hep-TA/Dex-TA mixtures at polymer concentrations of 10 or 20 wt % were prepared in vials at 37° C. In a typical procedure, to a PBS solution of Hep-TA (200 μL, 25 wt %), a freshly prepared PBS solution of $H_2O_2$ (25 μL of 0.3 wt % stock solution) and HRP (25 μL of 150 unit/mL stock solution) were added and the mixture was gently vortexed. The time to form a gel (denoted as gelation time) was determined using the vial tilting method. No flow within 1 min upon inverting the vial was regarded as the gel state.

Hydrogel Characterization

The heparin content of the Dex-TA/Hep-TA hydrogels was determined by a colorimetric method based on the binding of toluidine blue, with some modifications W L J Hinrichs et al. Journal of Controlled Release 1997; 45: 163-76.; M J B Wissink et al. Biomaterials 2001; 22: 151-63). Briefly, the hydrogels prepared at Dex-TA/Hep-TA weight ratio of 75/25, 50/50 and 25/75 were extracted in water and then freeze-dried. Samples (~1 mg) of dried gels were incubated overnight at room temperature in 2 ml of a 0.75 mg/ml 6 toluidine blue solution. Subsequently, the solutions were diluted 10 times with $H_2O$ and filtrated through 0.22 μm filter. The absorbance of the filtrations was measured at 630 nm. A standard curve was prepared by mixing 1 ml of known heparin solutions and 1 ml of 0.15 mg/ml toluidine blue solution in water at room temperature. After filtration through 0.22 μm filter, the absorbance of the solutions was measured at 630 nm. The heparin content in the hydrogels was calculated based on the heparin amount obtained from toluidine blue assay and the dry gel weight after extraction. For swelling tests, hydrogel samples (~0.25 mL) were prepared as described above and accurately weighted (Wi). Subsequently, 2 mL of PBS was applied on top of the hydrogels and then the samples were incubated at 37° C. for 72 h to reach the swelling equilibrium. The buffer solution was then removed from the samples and the hydrogels were weighted (Ws). The experiments were performed in triplicate and the equilibrium swelling ratio of the hydrogels was expressed as Ws/Wi. Rheological experiments were carried out with a MCR 301 rheometer (Anton Paar) using parallel plates (25 mm diameter, 0°) configuration at 37° C. in the oscillatory mode. A stock solution of Hep-TA/Dex-TA (600 μL, 25 wt % in PBS) at different weight ratios (100/0, 75/25, 50/50, 25/75 and 0/100) was mixed with 150 μL of an HRP/$H_2O_2$ mixture (75

μL of 150 unit/mL HRP and 75 μL of 0.3% $H_2O_2$) using a double syringe (2.5 mL, 4:1 volume ratio) equipped with a mixing chamber (Mixpac). After the samples were applied to the rheometer, the upper plate was immediately lowered to a measuring gap size of 0.5 mm, and the measurement was started. To prevent evaporation of water, a layer of oil was introduced around the polymer sample. A frequency of 0.5 Hz and a strain of 0.1% were applied in the analysis to maintain the linear viscoelastic regime. The measurement was continued up to the time the storage moduli recorded reached a plateau value. A frequency sweep and a strain sweep were also performed on the hydrogels from 0.1 to 10 Hz at a strain of 0.1%, and from 0.1 to 10% at a frequency of 0.5 Hz, respectively.

Chondrocyte Isolation and Incorporation

Bovine chondrocytes were isolated as previously reported (R Jin et al. Biomaterials 2009; 30: 2544-51) and cultured in chondrocyte expansion medium (DMEM with 10% heat inactivated fetal bovine serum, 1% Penincilin/Streptomicin (Gibco), 0.5 mg/mL fungizone (Gibco), 0.01 M MEM nonessential amino acids (Gibco), 10 mM HEPES and 0.04 mM L-proline) at 37° C. in a humidified atmosphere (95% air/5% $CO_2$). Hydrogels containing chondrocytes were prepared under sterile conditions by mixing a polymer/cell suspension with HRP/$H_2O_2$. Polymer solutions of Hep-TA/Dex-TA at different weight ratios (100/0, 75/25, 50/50, 25/75 or 0/100) were made in medium and HRP and $H_2O_2$ stock solutions were made in PBS. All the components were sterilized by filtration through filters with a pore size of 0.22 μm. Chondrocytes (P1) were incorporated in the hydrogels using the same procedure as in the absence of cells. The polymer final concentration was 20 wt % and the cell seeding density in the gels was $5\times10^6$ cells/mL. After gelation, the hydrogels (50 μL of each) were transferred to the culture plate and 2 mL of chondrocyte differentiation medium (DMEM with 0.1 μM dexamethasone (Sigma), 100 μg/mL sodium pyruvate (Sigma), 0.2 mM ascorbic acid, 50 mg/mL insulin-transferrin-selenite (ITS+1, Sigma), 100 U/ml penicillin, 100 μg/ml streptomycin, 10 ng/mL transforming growth factor β3 (TGF-β3, R&D System) was added. The samples were incubated at 37° C. in a humidified atmosphere containing 5% $CO_2$. The medium was replaced every 3 or 4 days.

Cell Viability and Proliferation

A viability study on chondrocytes incorporated in the hydrogels was performed with a Live-dead assay. At day 3, 7 and 14, the hydrogel constructs were rinsed with PBS and stained with calcein AM/ethidium homodimer using the Live-dead assay Kit (Invitrogen), according to the manufacturers' instructions. Hydrogel/cell constructs were visualized using a fluorescence microscope (Zeiss). Living cells fluoresce green and the nuclei of dead cells red. Quantification of total DNA of the constructs cultured for 1, 7, 14 and 21 days was done by CyQuant dye kit (Molecular Probes) using a fluorescent plate reader (Perkin-Elmer).

Swelling in the Presence of Chondrocytes

To evaluate the swelling behavior of hydrogels with chondrocytes incorporated, 50 μL of a gel/cell construct (Wsc) was incubated in medium at 37° C. in a humidified atmosphere containing 5% CO2. After 3 days, samples (n=3) were taken out of the medium and freeze-dried (Wdc). The degree of swelling was expressed as Wsc/Wdc.

RNA Extraction and Reverse Transcriptase-Polymerase Chain Reaction (RT-PCR)

After culturing the hydrogel/cell constructs in differentiation medium for 21 days, the samples were collected and washed with PBS. After disruption of the hydrogels, Trizol reagent (Invitrogen, Carlsbad, Calif.) was added to lysate the cells. Total RNA was isolated using the Nucleospin RNA II kit (Bloke) according to manufacturer's instructions. The RNA yields were determined based on the A260. Subsequently, the RNA (250 ng) was transcribed into single strand cDNA using the iScript Kit (BioRad) according to the manufacturer's recommendations. One microliter of each normalized cDNA sample was analyzed using the "SYBR Green PCR Core Kit" (Applied Biosystems) and a real-time PCR Cycler (BioRad). The expression of collagen type II and aggrecan (Table 1) was analyzed and normalized to the expression of the housekeeping gene glyceraldehyde-3-phosphate dehydrogenase (GAPDH). The efficiency of the single PCR reactions was determined and incorporated into the calculation.

Histological Staining

Samples cultured for 21 days were fixed in 10% formalin for 1 h. After embedding the samples in paraffin, 5 μm sections were collected and rehydrated with xylene and series of ethanol (from 100% 9 until 70%). The slides were left in distilled water for 10 minutes. Afterwards, toluidine blue (Fluka, 0,1% in deionized water) was added to the sections and left to incubate for 10 minutes. The slides were then washed with water and dehydrated. Sections were analyzed using a bright field microscope.

Matrix Production

The secretion of chondroitin sulfate and collagen type II by chondrocytes was evaluated by immunofluorescent staining. For biochemical analysis, the constructs cultured for 1, 7, 14 and 21 days were exposed to digestion using proteinase-K. The total collagen content was determined using the hydroxyproline assay (C A Edwards and W D O'Brien Jr. Clinica Chimica Acta 1980; 104: 161-7). The hydroxyproline content was determined via a colorimetric assay by reaction with chloramine T and dimethylaminobenzaldehyde. All values were corrected for the background staining of gels without cells. Data (n=3, measured in triplicate) are expressed as mean±standard deviation (SD).

Statistical Analysis

The experimental data between two groups were analyzed using a Student's t-test. Those among three or more groups were analyzed using One-way Analysis of Variance (ANOVA) with Turkey's post-hoc analysis. Statistical significance was set to a p value≤0.05. Results are presented as mean±standard deviation.

Hydrogel Characterization

Figure 3:
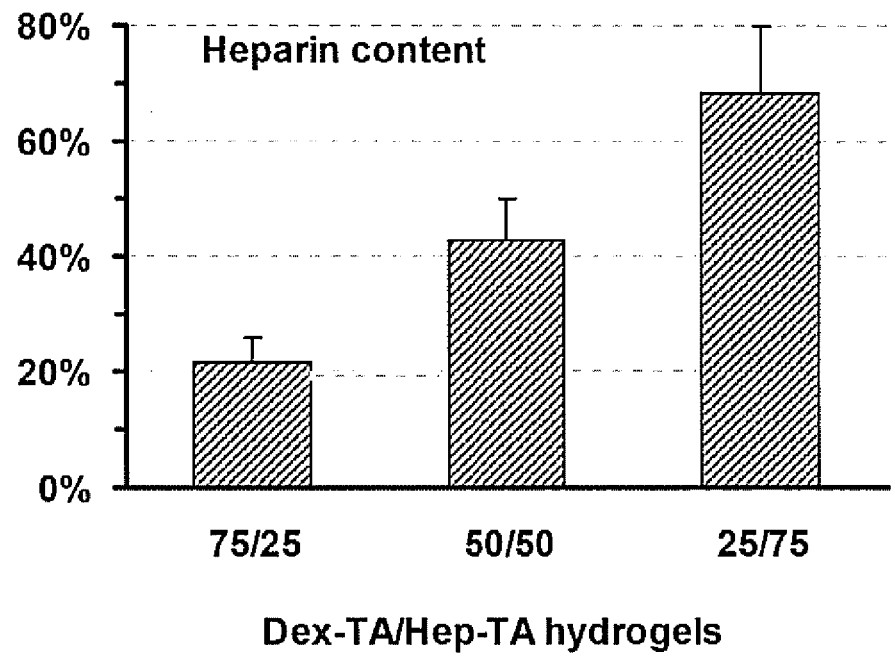
FIG. 3 shows the heparin-tyramine content in Dex-TA/Hep-TA hydrogels after extraction.
Figure 4:
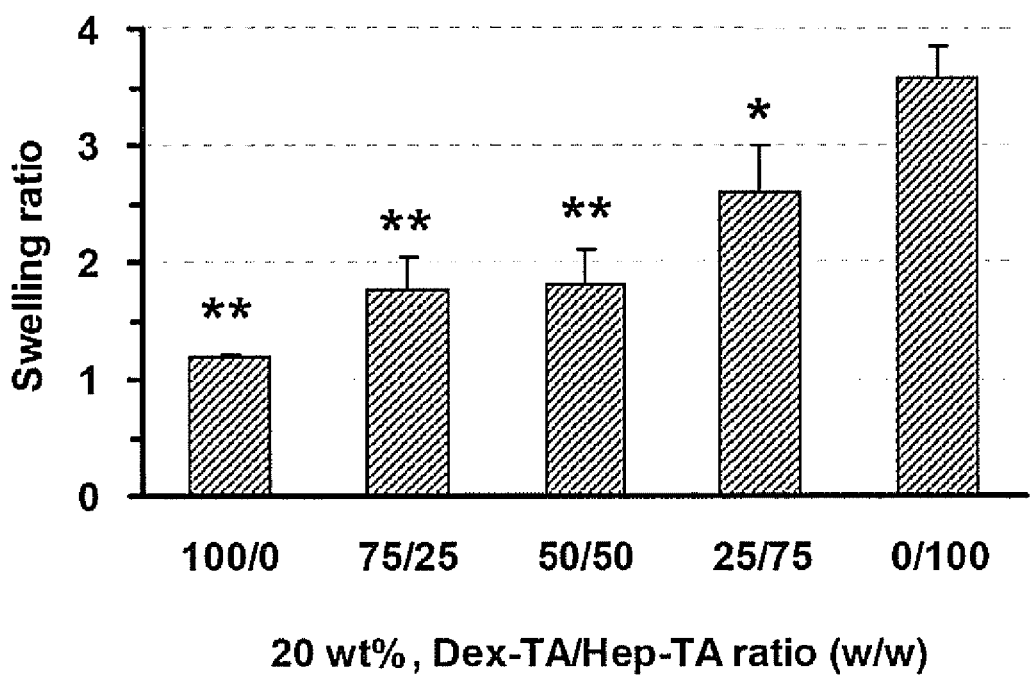
FIG. 4 shows equilibrium swelling ratios of Dex-TA/Hep-TA hydrogels. (*p<0.05; **p<0.01 vs. 0/100 gel)
Figure 11:
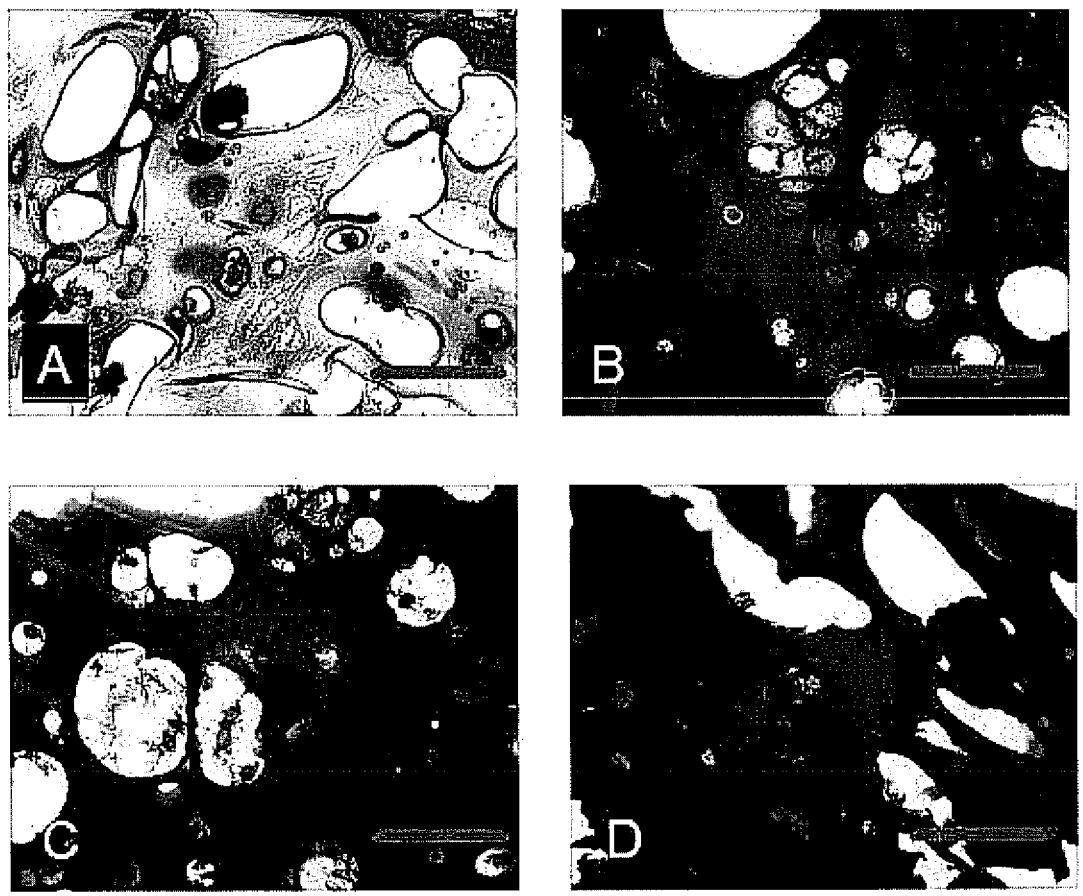
FIG. 11 shows a Toluidine blue staining of the hydrogels with Dex-TA/Hep-TA weight ratios of 100/0 (A), 75/25 (B), 50/50 (C) and 25/75 (D) after culturing for 21 days. Scale bar: 100 μm.

The incorporation of heparin in Dex-TA hydrogels was confirmed by a toluidine blue assay. The values of Hep-TA content were close to the theoretical values at which the gels were prepared (FIG. 11 3b). This indicated that Hep-TA conjugates were successfully co-crosslinked with Dex-TA conjugates to form a hydrogel. The swelling ratios of 20 wt % hydrogels at different Dex-TA/Hep-TA weight ratios are shown in FIG. 4. The Hep-TA hydrogels had a higher swelling ratio than the Dex-TA hydrogel (3.6 vs. 1.2).

Cell Migration Experiments

Hop-TA 25% was mixed in a ratio of 75/25, 50/50 and 25/75 with Dex-TA 25% and horse radish peroxidase and $H_2O_2$ were added to a final volume of 50 μL to induce gelation. The hydrogels were placed in the bottom of a CytoSelect 24-well cell migration plate (Kit CytoSelect 24-well Cell Migration Assay 8 μm, Colorimetric format; CBA-100 Cell Biolabs, Inc.). A volume of 300 μL of a cell suspension, containing 2 million cells/ml in serum free media, was added to the inside of each insert and incubated for 24 hours. Afterwards, the media was carefully aspirated from the inside of the insert. The interior of the inserts was swabbed to remove the non-migratory cells. The inserts were transferred to a clean well containing 400 μL of Cell Stain Solution and incubated for 10 minutes at room temperature. The stained inserts were washed several times and allowed to air dry. Each insert was transferred to an empty well and 200 μL of Extraction Solution were added. After 10 minutes of incubation on an orbital shaker, 100 μL from each sample were transferred to a 96-well microtiter plate and the OD 560 nm was measured in a plate reader.

Figure 15:
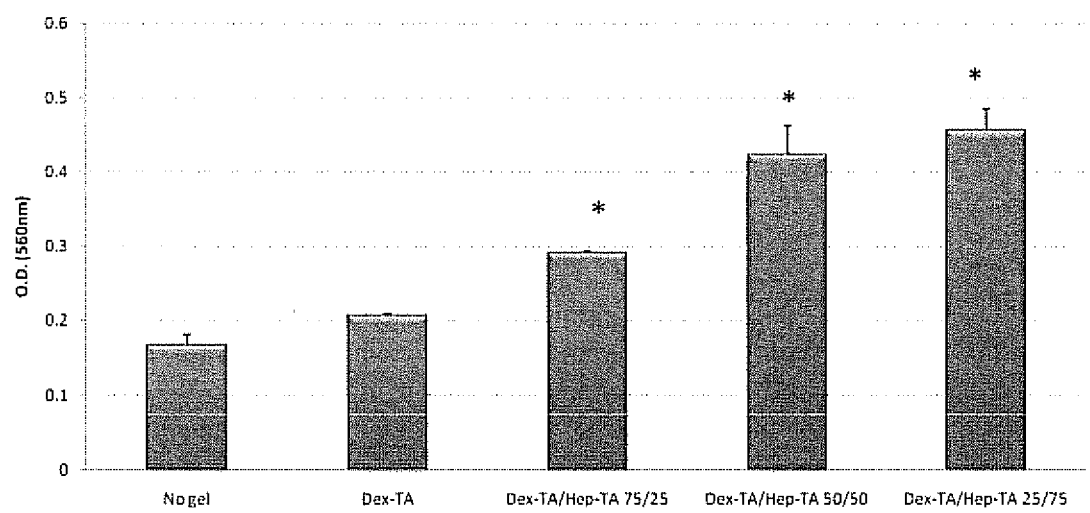
FIG. 15 shows the effect of different ratios of Dex-TA and Hep-TA on migration of bovine chondrocytes. The migration of bovine chondrocytes was assessed using a Cell migration assay according to manufacturer's instructions (Cytoselect migration assay kit). Similar data were found using human Mesenchymal Stem Cells (hMSCs) or human chondrogenic progenitor cells (CPCs) (data not shown)
Figure 16:
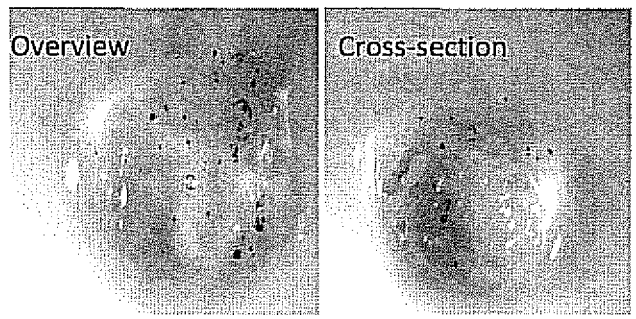
FIG. 16 illustrates the cell homing of bovine chondrocytes induced by a Hep-TA hydrogel.
Figure 16:
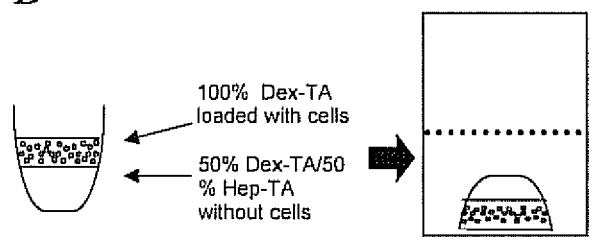
Figure 16:
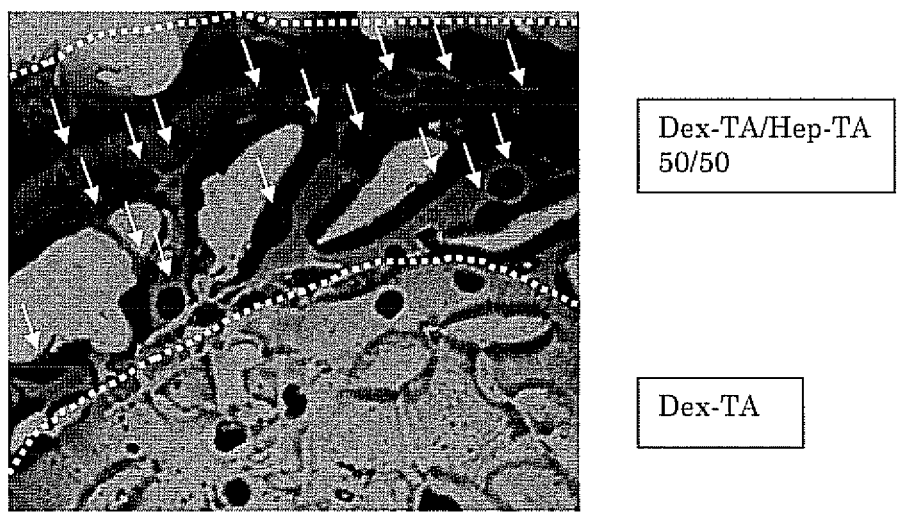

From FIGS. 15 and 16 it is concluded that the ratio of Hep-TA/Dex-TA relates to the cell attracting properties of the hydrogel: hydrogels containing no Hep-TA have attracted a lower number of cells than hydrogels wherein Hep-TA is present and increasing the ratio between the ratio between Hep-TA/Dex-TA results in more migration of cells. In the cell migration assay, Dex-TA hydrogels were used as comparison and no significant difference was observed when compared to the control without gel. With increasing ratios of Hep-TA, progressively more cell migration is observed, suggesting that these hydrogels can induce a cell homing effect. This effect was found using chondrocytes, human mesenchymal stem cells and chondrogenic progenitor cells. This demonstrates that Dex-TA/Hep-TA hydrogels are very suitable for use as a cell free hydrogel construct that can be applied on a damaged cartilage surface. This hydrogel can subsequently attract cells from the surrounding cartilage, synovium, bone marrow or synovial fluid that can growth into the hydrogel and repair the damaged surface. Cell from the synovial fluid and/or bone marrow can migrate into Dex-TA/Hep-TA hydrogel, allowing matrix to be produced within the hydrogel.

In agreement to the induced cell attracting potential of Dex-TA/Hep-TA hydrogels assessed by a porous membrane assay, cell homing and ingrowth was also observed within the hydrogels. FIG. 16-A shows that the chondrocytes are able to adhere and migrate into Dex-TA/Hep-TA hydrogels. To further evaluate if Dex-TA/Hep-TA hydrogels stimulate cell migration, a two layered hydrogel construct was assembled, with one layer of 100% Dex-TA seeded with cells and the other layer of Dex-TA/Hep-TA 50/50 without cells. After one week in culture, cells have migrated from the Dex-TA layer into the Dex-TA/Hep-TA hydrogels (FIG. 16B-C). This proves that Dex-TA/Hep-TA containing hydrogels can attract cells and stimulate their ingrowth in the hydrogel construct.

The invention claimed is:

1. A composition comprising a dextran-tyramine (Dex-TA) conjugate and a conjugate selected from the group consisting of chondroitin sulphate-tyramne, collagen-tyramine, chitosan-tyramine, chitosan-phioretic acid, gelatine-tyramine, heparan sulphate-tyramine, karatan sulphate-tyramine, hyaluronic acid-tyramine and heparin-tyramine (Hep-TA);
   wherein Dex-TA and Hep-TA, if present, are present in a weight ratio between 95:5 and 5:95.

2. A composition according to claim 1, wherein said composition comprises a Hep-TA conjugate and a Dex-TA conjugate.

3. A composition according to claim 2, wherein Dex-TA and Hep-TA are present in a weight ratio between 25:75 and 80:20.

4. A composition according to claim 1, further comprising a suitable amount of hydrogen peroxide and suitable amount of a peroxidase.

5. A composition according to claim according to claim 1, wherein the amount of the heparin-tyramine (Hep-TA) conjugate of the composition if present, is between 10 and 20 wt % based on the weight of the composition.

6. A composition according to claim 4, wherein the concentration of peroxidase is between 10-125 Units/ml.

7. A composition according to claim 4, wherein the concentration of hydrogen peroxide is between 0.005 and 0.05 M.

8. A composition according to claim 4 in the form of an injectable hydrogel.

9. A composition according to claim 1 further comprising cells.

10. A composition according to claim 1 further comprising a growth factor.

11. A composition according to claim 1 further comprising a medicament.

12. A method of treating a subject in need thereof by administering to said subject a composition according to claim 1.

13. A kit comprising a dextran-tyramine conjugate and a conjugate selected from the group consisting of chondroitin sulphate-tyramine, collagen-tyramine, chitosan-tyramine, chitosan-phloretic acid, gelatine-tyramine, heparan sulphate-tyramine, keratan sulphate-tyramine, hyaluronic acid-tyramine and heparin-tyramine and optionally a peroxidase, hydrogen peroxide and/or an instruction for preparing an injectable hydrogel according to claim 8.

14. Kit according to claim 13, wherein said kit comprises Dex-TA and Hep-TA and optionally a peroxidase, hydrogen peroxide and/or an instruction.

15. Method of producing a hydrogel, said method comprising the step of curing the composition according to claim 1, wherein said composition comprises a curing amount of peroxide and a peroxidase.

16. Hydrogel obtainable by the method of claim 15.

17. A polymer of a dextran-tyramine conjugate and a conjugate selected from the group consisting of chondroitin sulphate-tyramine, collagen-tyramine, chitosan-tyramine, chitosan-phloretic acid, gelatine-tyramine, heparan sulphate-tyramine, keratan sulphate-tyramine, hyaluronic acid-tyramine and heparin-tyramine;
   wherein said polymer is obtainable by crosslinking said tyramines in said conjugates.

18. Polymer according to claim 17, wherein said polymer is of a heparin-tyramine (Hep-TA) conjugate and a dextran-tyramine conjugate (Dex-TA).

19. A composition according to claim 9 further comprising stem cells and/or chondrocytes.

20. A composition according to claim 19 wherein said stem cells are mesenchymal stem cells, embryonic stem cells or pluripotent stem cells, or a combination of different stem cells.

21. A composition according to claim 10, where the growth factor is Bone Morphogenetic Protein (BMP) or a Transforming Growth Factor beta (TGF-β).

* * * * *

UNITED STATES PATENT AND TRADEMARK OFFICE
CERTIFICATE OF CORRECTION

PATENT NO. : 9,132,201 B2
APPLICATION NO. : 13/509365
DATED : September 15, 2015
INVENTOR(S) : Hermanus Bernardus Johannes Karperien et al.

It is certified that error appears in the above-identified patent and that said Letters Patent is hereby corrected as shown below:

On the title page, item (73), assignee reads: "UNIVERSITY OF TWENTE, INSTITUTE FOR BIOMEDICAL AND TECHNICAL MEDICINE (MIRA), Enschede (NL)", Should read --UNIVERSITY OF TWENTE, INSTITUTE FOR BIOMEDICAL TECHNOLOGY AND TECHNICAL MEDICINE (MIRA), Enschede (NL)--

Signed and Sealed this
Thirty-first Day of May, 2016

Michelle K. Lee
*Director of the United States Patent and Trademark Office*